United States Patent [19]

Lagow

[11] 3,983,182
[45] Sept. 28, 1976

[54] ALKALI METAL ORGANIC COMPOUNDS AND THEIR METHOD OF PREPARATION

[75] Inventor: Richard J. Lagow, Manchester, Mass.

[73] Assignee: Massachusetts Institute of Technology, Cambridge, Mass.

[22] Filed: Aug. 23, 1973

[21] Appl. No.: 391,035

Related U.S. Application Data

[63] Continuation-in-part of Ser. No. 286,261, Sept. 5, 1972, abandoned.

[52] U.S. Cl. .................. 260/665 R; 260/448.2 E; 260/448.2 R; 260/666 P; 260/668 R; 260/676 R; 260/677 R; 423/439

[51] Int. Cl.² ..................... C07F 1/02; C07F 1/04; C07F 1/00

[58] Field of Search .................. 423/439; 260/665 R

[56] References Cited
UNITED STATES PATENTS

| | | | |
|---|---|---|---|
| 2,087,656 | 7/1937 | Rice | 260/665 |
| 2,474,021 | 6/1949 | Vining | 423/646 |
| 2,948,762 | 8/1960 | Muench et al. | 260/665 |

OTHER PUBLICATIONS von Hartel et al., Chem. Abst. 27 (1933) p. 221.
Parrish et al., J. Chem. Phys. 1971 (54) pp. 2518-2528.
Chung et al. Chem. Abst. 77 (1972) No. 164787C.
Bagouin et al. Compte Rendue. 262C (1966) pp. 557–559.
Roessler et al. Sodium, Roessler & Hasslacker Co., N.Y. 1931, pp. 53, 58-72.
Salzano et al., Am. Ceramics Soc. 51 (1968) p. 465.
Kaufman et al. J. Phys. Chem. 67 (1963) pp. 896-902.

*Primary Examiner*—Arthur P. Demers
*Attorney, Agent, or Firm*—Arthur A. Smith, Jr.; Paul J. Cook; Martin M. Santa

[57] ABSTRACT

Alkali metal organic compounds including perlithiated organic compounds are produced by contacting an organic compound having a carbon to hydrogen bond or a carbon to halogen bond in its molecular structure or carbon vapor with a vaporous alkali metal under dry conditions and in the absence of a gas that reacts with the alkali metal other than the organic compound. The alkali metal is activated such as thermally or by being passed through a radio frequency field so that it has sufficient energy to break at least one of the bonds. Perlithiated compounds are formed from alkanes, alkenes, cycloalkanes and aromatic hydrocarbons.

33 Claims, No Drawings

ALKALI METAL ORGANIC COMPOUNDS AND THEIR METHOD OF PREPARATION

The invention herein described was made in the course of work performed under a contract with the Advanced Research Projects Agency, Department of the Army.

REFERENCE TO RELATED APPLICATIONS

This application is a continuation-in-part of application Ser. No. 286,261, filed Sept. 5, 1972, now abandoned.

BACKGROUND OF THE INVENTION

The invention relates to a process for forming alkali metal organic compounds and to the alkali metal organic compounds produced; particularly the poly lithium organic compounds produced.

Presently, organolithium compounds are of interest since they are effective polymerization initiators for monoolefins or conjugated diolefins. Polylithium compounds now are prepared by reacting a polyhalogenated hydrocarbon with lithium in a solvent. These processes are undesirable for a variety of reasons. In many instances, reactive intermediates such as dihalocarbenes are formed which react with the solvent employed to form undesirable by-products. In other reactions, it is difficult to remove the solvent completely from the product which, in the case of ether solvents, is undesirable since they adversely affect polymerization of olefins when the lithium product is employed as a polymerization initiator. Furthermore, when lithium compounds are formed from alkylene dihalides and lithium, the lithiated product reacts with the dihalide to form higher alkylene chains and cycloalkanes thereby reducing the yield of desired product. Perlithiated products have not been produced by present processes employing an organic halide reactant.

Lithiated organic compounds also are produced by reacting, in a solvent, n-butyllithium with an alkyne such as propyne or butyne. Unfortunately, this process cannot be employed to form lithiated products from organic compounds other than alkynes.

It would be highly desirable to provide per (alkali metal) organic compounds, particularly perlithium organic compounds and methods for their preparation. These compounds would be useful in a wide variety of reactions such as those now employing Gringard reagents for organic compound syntheses. For example, per lithium compounds are reactive with halogenated organic or inorganic halides or polyhalides to form alkali metal halide and bind the lithiated carbon atom to the site of the halide reactant formerly occupied by the halogen atom. In this manner, any number of carbon atoms, acyclic or cyclic, could be added to a wide variety of reactive sites. Furthermore, these compounds are useful to crosslink halogen-containing polymers such as poly vinyl chloride to form crosslinked polymers having a wide diversity of crosslink "bridges."

SUMMARY OF THE INVENTION

The present invention provides a process for forming alkali metal organic compounds by reacting with a vaporous alkali metal with carbon vapor or with an organic hydrocarbon or halogenated hydrocarbon having a carbon to hydrogen bond or a carbon to halogen bond to replace the hydrogen or halogen atom with an alkali metal. The reaction can be conducted with organic compounds in solid or vapor form and which are solid, liquid or gas at normal atmospheric conditions. The reaction is conducted in a dry atmosphere substantially free of gases that react with lithium above about 600°C such as free oxygen and nitrogen to prevent degradation of the product. The energy needed to effect reaction is supplied thermally by heating the reactants, generally from the temperature at which the alkali metal vaporizes up to the temperature at which the organic reactant or product experiences significant thermal degradation and/or by exciting the orbital electrons of the alkali metal or of the halogen or hydrogen atoms of the organic reactant such as by passing them through a radio frequency field prior to or during reaction. The alkali metal organic product is recovered as a solid. This invention also provides novel alkali metal organic compounds including per (alkali metal) compounds not obtainable by prior art processes such as perlithiated alkanes represented by the formula:

wherein $n$ is at least 1, perlithiated olefins represented by the formula:

wherein $n$ is at least 2, perlithiated aromatic compounds, perlithiated cycloalkanes and polylithiated cyclic and acyclic organic compounds and polymers.

DESCRIPTION OF PREFERRED EMBODIMENTS

This invention will be described hereinafter with reference to lithium as the alkali metal reagent. It is to be understood that this invention also can be carried out with sodium or potassium rather than lithium. Reaction is effected by contacting vaporized lithium with carbon vapor or hydrocarbon or halohydrocarbon in solid or vaporous form in a dry non-oxidizing atmosphere. Reaction occurs either under vacuum of less than about $10^{-2}$ preferably less than $10^{-4}$ torr or in an inert atmosphere such as helium, argon, neon, krypton, xenon or the like. The mole ratio of lithium to moles of the reactive carbon vapor, carbon to hydrogen bond and/or carbon to halogen bond when initiating reaction, is above about 2 to 1 preferably about 5 to 1 in order to effect as complete substitution as possible of lithium atoms for hydrogen or halogen atoms of the organic compound at the energy level to which the reactants are raised during or prior to reaction. The product is recovered by condensation from the reaction mixture which can be effected conveniently by providing a cold solid surface in the reaction zones. In the case where a solid organic material is employed as the reactant, it can comprise the cold solid surface.

The degree of lithium substitution is controlled primarily by the mole ratio of lithium to organic reactant and by the energy level to which the reactants are raised prior to and during reaction. In the case where the heated lithium atom replaces a hydrogen atom of the organic reactant, an activation energy of above about 20 kilocalories per mole of lithium is needed to initiate reaction. This energy can be supplied by heating the lithium to temperatures above 600°C, but less than that which causes thermal degradation of the organic reactant, passing the vaporized lithium through a radio frequency field to excite the lithium atoms, heating the organic reactant but to a temperature less than that which causes substantial undesirable thermal degradation of passing the organic reactant through a radio frequency field to excite the organic molecule or a combination of these techniques. In the case where the lithium atom is employed to replace a halogen atom of the organic reactant, far less energy per mole of lithium is needed so that these reactions can be conducted either at lower temperatures or without the use of a radio frequency field through which either of the reactants pass. When the alkali metal and carbon are contacted when each is in the vapor state, there is sufficient activation energy to effect the desired reaction. The reactants can be subjected to a radio frequency field by means of a radio frequency generator which can generate up to about 30Kw. Other suitable methods for activating the reactants to high energy levels include microwaves, ultraviolet radiation, and conventional radiation sources such as x-rays, gamma rays or high energy electrons. In the case where a halogenated hydrocarbon reactant is employed, the excess lithium present substantially reduces undesirable side reactions wherein partially lithiated products react with the halogenated hydrocarbon reactant.

It is preferred to conduct the reaction in a vacuum since the presence of an inert gas in the reaction chamber reduces the mean free path of the lithium atoms thereby requiring higher lithium vapor temperatures to effect a given reaction rate. When employing a vacuum, the reactor is evacuated to a pressure of at least $10^{-2}$ torr in order to remove substantial amounts of the free oxygen and nitrogen therefrom.

In conducting the reaction, the lithium metal is vaporized into the reaction zone at a temperature of at least 600°C preferably from 800° to 1000°C while carbon vapor or a vaporous organic hydrocarbon or halohydrocarbon is passed into the reaction zone at any temperature above which it is maintained as a vapor. While higher temperatures may be employed, the increased reaction rate obtained thereby is insufficient to justify increased heating costs. For example, normally gaseous organic reactants can be passed into the reaction zone at room temperature while normally liquid organic reactants need be heated only to a temperature at which they vaporize. When employing a normally solid organic reactant, it is suspended in the reaction zone so that the surfaces of the solid react with the lithium to form lithiated compounds or it can be vaporized in the reactor.

The compounds of the invention are recovered in admixture with lithium and with other polylithiated compounds when employing halogenated reactants or with monolithiated or polylithiated compounds when employing a hydrocarbon reactant.

Any cyclic or acyclic organic reactant can be employed including straight and branched chain alkanes, alkenes, and alkynes; cycloalkanes, cycloalkenes, aromatic hydrocarbons, condensed ring aromatic hydrocarbons, halogenated alkanes, halogenated alkenes, halogenated alkynes, halogenated cycloalkanes, halogenated cycloalkenes, halogenated aromatic hydrocarbons, halogenated condensed ring aromatic hydrocarbons as well as polymeric halogenated hydrocarbons or hydrocarbons.

While the invention has been described above with reference to a one step contact of the organic reactant with vaporous lithium, it is to be understood that the process of this invention can be conducted in a two step procedure wherein vaporous lithium is contacted with a halogenated hydrocarbon to replace the halogen atoms with lithium and recovering the lithiated product. Thereafter, the partially lithiated product can be vaporized and reacted with vaporous lithium at the more severe conditions necessary to break the carbon to hydrogen bonds of the product and subsequently to form a carbon to lithium bond.

By employing the process of this invention, perlithiated organic compounds are produced from reactants other than alkynes for the first time. For example, tetralithiomethane is produced from methane or carbon tetrachloride, hexalithioethane is produced from ethane or hexachloroethane, hexalithiobenzene is produced from benzene, perlithioadamantane is produced from adamantane and tetralithioethylene is produced from ethylene or ethylene tetrachloride.

In addition, the process of this invention is useful to produce novel partially lithiated organic compounds. Thus, when employing an organic reactant having both carbon to halogen bonds and carbon to hydrogen bonds in its molecular structure, vaporous lithium atoms at relatively low energy levels will replace the halogen atoms of the organic reactant molecule in preference to the hydrogen atoms due to the lower energy requirements for the alkali metal-halogen replacement. In addition, partially lithiated compounds can be formed from a hydrocarbon having in its molecular structure a plurality of carbon to hydrogen bonds where some carbon atoms are in a $sp^3$ hybridized state and others are in the sp or $sp^2$ states. When these compounds are reacted with vaporous lithium, the lithium preferentially replaces the hydrogen bonded to the sp or $sp^2$ hybridized carbon atoms due to the reduced energy required for this replacement as compared to the energy required to break the bonds with the $sp^3$ carbon atoms. For example, cyclohexadiene has a plurality of carbon to hydrogen bonds formed from both $sp^2$ and $sp^3$ hybridized carbon atoms. When vaporous lithium heated to about 1000°C, the primary product formed is 2, 3, 5, 6 tetralithio cyclohexadiene.

The following examples illustrate the present invention and are not intended to limit the same.

EXAMPLE I

Eleven grams of high purity lithium metal under argon was placed in a Knudson cell and the apparatus was evacuated to a pressure of at least $10^{-5}$ torr for 10 to 12 hours. The Knudson cell was 6 inches high and had an inside diameter of 1 ½ inches. The vaporized lithium passed from the Knudson cell into a stainless steel reactor 11 ¾ inches high and having an inside diameter of 5 inches. A stainless steel cylinder extended from the top inside surface of the reactor 9 ½ inches and had an outside diameter of 4 inches. The cylinder was cooled to about 196°C by circulating liquid nitrogen therein. An inlet conduit for delivering organic reactant into the reactor was provided adjacent to the bottom inside surface of the reactor.

Lithium vapor was formed by heating the Knudson cell resistively at 800° to 850°C to vaporize all of the lithium therein. About 1.5 grams of carbon tetrachloride was introduced into the reactor at a temperature of about 20°C over a period of 30 to 45 minutes. Thereafter, the reactor was cooled and the liquid nitrogen in the cylinder was evaporated. The system was pumped down to $10^{-5}$ torr with a cold trap for several hours to remove any traces of carbon tetrachloride. No carbon tetrachloride was recovered. The reactor then was filled with argon, sealed and transferred to a dry box. The produce was a brittle gray-white solid condensed on the outside surface of the cylinder and was removed therefrom and stored in a glass vacuum vessel. The product was extremely air and moisture sensitive and in contrast to lithium exploded violently producing flames on contact with water. The product was stable for at least 4 months when sealed under argon.

It was found that the product could be stored for months sealed under argon without decomposition. The reaction product was removed and weighed under argon and was transferred to a vacuum line and hydrolyzed with $D_2O$ at 0°C. The hydrolysis products were passed through a −78°C trap to remove $D_2O$ and collected at −196°C. The products were then expanded into a gas phase molecular weight apparatus for a mass balance measurement and then collected at −196°C.

The total yield of products varied from 95 to 99% based on the amount of $CCl_4$ used. A small amount of carbon was recovered after hydrolysis which ranged from 0.5 to 4%. The products were then separated, collected, and characterized using a high resolution double focusing C.E.C. -21-110B mass spectrometer and again on a Hitachi RMU-6 mass spectrometer both at 70ev. Strong parent ions were observed for $CD_4^+$ (20.05639) $C_2D_4^+$ (32.05640) and $C_2D_2^+$ (28.02819). The yield of $CD_4$ ranged from 10–18% based on $CCl_4$ and averaged about 14% (1m mole). The average yield of $C_2D_4$ was 61% (3.4m moles) and the average yield of $C_2D_2$ was 20% (1.1m moles).

To further characterize the reactive solid and to demonstrate that the species would react as one would expect for organolithium species, the material was derivatized with chlorotrimethylsilane. A sample of the product was broken into small pieces under argon in a dry box and placed in a 50 ml round bottom flask. As excess of $ClSiMe_3$ (4–6 ml) was added and the mixture was stirred continuously at room temperature overnight. The excess $ClSiMe_3$ was removed by pumping and the remaining solid was recovered for spectroscopic work. Using $CHCl_3$ as an internal reference the $H^1$N.M.R. contained a singlet at T = 9.80 which is an agreement with the spectra reported for $C(SiMe_3)_4$. The mass spectrum contained a parent peak at 304 and a $P-(CH_3)$ peak for $C(SiMe_3)_4$ with the proper silicone isotope distributions. $C_2(SiMe_3)_4$ was also produced and was characterized by a parent peak at 316 with a silicon isotope pattern and a singlet in the N.M.R.

EXAMPLE II

Employing the apparatus described in example 1, 1.5 grams of hexachloroethane was reacted with 11 grams of lithium vapor heated to a temperature of 800° to 850°C. The product was condensed on the outside surface of the cooled cylinder. The product was recovered as described in Example I and thereafter hydrolyzed with $D_2O$. The several experiments the hydrolysis product was entirely $C_2D_6$, and the mass spectra contained a parent ion $C_2D_6^+$ (36.08444), $C_2D_5^+$ (34.07010), $CD_3^+$ (18.02294) and $CD_2^+$ (16.02842). The yields averaged 80% based on $C_2Cl_6$ (5.1m moles $C_2D_6$). In other experiments where it appeared that the lithium vapor concentration was about 30% less, from 10 to 20 percent $C_2D_4^+$ and $C_2D_2^+$ were observed and the total yield of deuterated products was still 80%. The solid was also reacted with $ClSiMe_3$ and a small amount of solid product was recovered and characterized by mass spectroscopy and $H^1$ N.M.R. A strong peak was observed for $C(SiMe_3)_3^+$ at 231 with the proper silicon isotope pattern. A singlet in the methylsilane region was also observed in the N.M.R. spectra of the material. It is not surprising that no parent ion is seen for $C_2(SiMe_3)_6$ due to the high degree of steric interference of the trimethylsilyl groups.

EXAMPLE III

Employing the apparatus described in Example I, 1.5 grams of butadiene was reacted with 11 grams of lithium which was vaporized at a temperature of 800° to 850°C. The product was condensed on the outside surface of the cooled cylinder, was recovered as described in Example I and thereafter hydrolyzed with $D_2O$. The deuterated product was characterized by mass spectroscopy which revealed a parent ion for $C_4D_6^+$. The precursor for this ion is $C_4Li_6$.

EXAMPLE IV

Employing the apparatus described in Example I, 1.5 grams of trichlorobenzene was reacted with 11 grams of lithium which was vaporized at a temperature of 800° to 850°C. The product was condensed on the outside surface of the cooled cylinder, was recovered as described in Example I and thereafter hydrolyzed with $D_2O$. The deuterated product was characterized by mass spectroscopy which revealed a parent ion for $C_6D_3H_3^+$ The precursor for this ion is $C_6Li_3H_3$.

EXAMPLE V

Employing the apparatus described in Example I, 1.5 grams of naphthalene was reacted with 11 grams of lithium which was vaporized at a temperature of 800° to 850°C. The product was condensed on the outside surface of the cooled cylinder, was recovered as described in Example I and thereafter hydrolyzed with $D_2O$. The deuterated product was characterized by mass spectroscopy which revealed a parent ion for $C_{10}D_8^+$. The precursor for this ion is $C_{10}Li_8$.

EXAMPLE VI

Employing the apparatus described in Example I, 1.5 grams of benzene was reacted with 11 grams of lithium which was vaporized at a temperature of 800° to 850°C. The product was condensed on the outside surface of the cooled cylinder, was recovered as described in Example I and thereafter hydrolyzed with $D_2O$. The deuterated product was characterized by mass spectroscopy which revealed a parent ion for $C_6D_6^+$. The precursor for this ion is $C_6Li_6$. The yield of $C_6Li_6$ was about 10% and was obtained in admixture with lithium benzene and other polylithiated benzene species.

EXAMPLE VII

Employing the apparatus described in Example I, 1.5 grams of cyclohexadiene was reacted with 11 grams of lithium which was vaporized at a temperature of 800° to 850°C. The product was condensed on the outside surface of the cooled cylinder, was recovered as described in Example I and thereafter hydrolyzed with $D_2O$. The deuterated product was characterized by mass spectroscopy which revealed a parent ion for $C_6D_4H_4^+$. The precursor for this ion is $C_6Li_4H_4$.

EXAMPLE VIII

Employing the apparatus of Example I but including a stainless steel reactor in which carbon vapor was generated by an arc between movable graphite electrodes positioned at the orifice of the lithium Knudsen cell carbon vapor and lithium vapor were reacted. The reaction vessel was evacuated to $10^{+5}$ Torr, and the Knudsen cell, containing 11 g of lithium, was heated to 800°–850°C by induction or resistance heating. The lower walls of the reactor were cooled to −196°C, and the arc was initiated with an 18-V, 250-A ac source. After 45 min. the reaction was terminated. The extremely air- and moisture-sensitive products were handled with care under argon.

The products were hydrolyzed at 0°C, passed through a trap at −30°C to remove $H_2O$ and collected at −196°C. The yield (gas measurement) of gaseous products averaged 11 mmol/45 min. The hydrolysis products were characterized using a high-resolution double-focusing C.E.C.-21-110B mass spectrometer at 70eV. Parent ions were observed for $CH_4^+$ (16.03133), $C_2H_2^+$ (26.01671), $C_2H_4^+$ (28.03081), and $C_3H_4^+$ (40.03177). The principal product, $C_3H_4$ ranged from 40 to 65% of the volatile products. Percentage yields of other hydrocarbons were $CH_4$, 0–10%, and $C_2H_2$, 10–30%. The yield of $C_2H_4$ averaged 15%, but occasionally accounted for 45% of the volatile products. Spectroscopic quantities of several higher molecular weight products were also observed.

The principal product, $C_3Li_4$, which is known to be soluble in THF, was then derivatized by adding $ClSi(Me_3)_3$ to a −78°C THF solution of the reaction product and warmed while stirring over a 24 hour period. A white compound, $C_3(SiMe_3)_4$, was recovered and was characterized by its mass and nmr spectra. A parent ion was observed at 328 and a $(P-CH_3)^+$ peak occurred at 313 with the appropriate silicone isotopic distributions. The $H^1$ nmr spectrum of the compound in $CCl_4$ gave a singlet at 9.89 which is in agreement with the spectrum previously reported (9.90) for $C_3(SiMe_3)_4$.

I claim:

1. A process for forming an alkali metal organic compound which comprises contacting an organic reactant selected from the group consisting of carbon vapor and an organic compound having a carbon to hydrogen bond or a carbon to halogen bond with a vaporous alkali metal under dry conditions and in the substantial absence of a gas that reacts with the alkali metal other than the organic reactant, said alkali metal having sufficient energy to react with the carbon vapor or to break at least one of said bonds.

2. The process of claim 1 wherein said organic compound is an alkane.

3. The process of claim 1 wherein said organic compound is an alkene.

4. The process of claim 1 wherein the organic compound is an aromatic hydrocarbon.

5. The properties of claim 1 wherein the organic reactant is halogenated alkane and the mole ratio of alkali metal to reactive carbon to halogen bonds is at least about 2:1.

6. The process of claim 1 wherein the organic compound is a halogenated alkene and the mole ratio of alkali metal to reactive carbon to halogen bonds is at least 2:1.

7. The process of claim 1 wherein the organic compound is a halogenated aromatic hydrocarbon and the mole ratio of alkali metal to reactive carbon to halogen bonds is at least 2:1.

8. The process of claim 1 wherein said organic compound is a halogen-containing polymer.

9. The process of claim 1 wherein said organic compound is a hydrocarbon polymer.

10. The process of claim 1 wherein the alkali metal is lithium.

11. The process of claim 2 wherein the alkali metal is lithium.

12. The process of claim 3 wherein the alkali metal is lithium.

13. The process of claim 4 wherein the alkali metal is lithium.

14. The process of claim 5 wherein the alkali metal is lithium.

15. The process of claim 6 wherein the alkali metal is lithium.

16. The process of claim 7 wherein the alkali metal is lithium.

17. The process of claim 8 wherein the alkali metal is lithium.

18. The process of claim 9 wherein the alkali metal is lithium.

19. Tetralithiomethane

20. Hexalithioethane

21. Hexalithiobenzene

22. Tetralithioethylene

23. Perlithioadamantane

24. A compound of the formula:

$$C_n M_{2n+2}$$

wherein $n$ is at least 1 and M is selected from the group consisting of sodium, lithium and potassium.

25. A compound of the formula:

$$C_n M_{2n}$$

wherein $n$ is at least 2 and M is selected from the group consisting of sodium, lithium and potassium.

26. The compound of claim 25 comprising a mono-olefin.

27. The compound of claim 25 comprising a cycloalkane.

28. A per (alkali metal) aromatic organic compound wherein the alkali metal is selected from the group consisting of sodium, lithium and potassium.

29. The compound of claim 24 wherein M is lithium.

30. The compound of claim 25 wherein M is lithium.

31. The compound of claim 26 wherein M is lithium.

32. The compound of claim 27 wherein M is lithium.

33. The compound of claim 28 wherein the alkali metal is lithium.

* * * * *